(12) United States Patent
Hayes et al.

(10) Patent No.: US 7,375,049 B2
(45) Date of Patent: May 20, 2008

(54) CATALYST

(75) Inventors: Martin John Hayes, Royston (GB);
Chandresh Malde, Reading (GB);
Michael Ian Petch, Reading (GB);
Stephen David Pollington, Tyne and Wear (GB); Brian Ronald Charles Theobald, Reading (GB)

(73) Assignee: Johnson Matthey PLC, London (GB)

( * ) Notice: Subject to any disclaimer, the term of this patent is extended or adjusted under 35 U.S.C. 154(b) by 65 days.

(21) Appl. No.: 10/486,622

(22) PCT Filed: Jul. 15, 2002

(86) PCT No.: PCT/GB02/03218

§ 371 (c)(1),
(2), (4) Date: Aug. 9, 2004

(87) PCT Pub. No.: WO03/013728

PCT Pub. Date: Feb. 20, 2003

(65) Prior Publication Data

US 2004/0266612 A1  Dec. 30, 2004

(30) Foreign Application Priority Data

Aug. 8, 2001 (GB) .................... 0119327.5

(51) Int. Cl.
*B01J 21/18* (2006.01)
*B01J 23/40* (2006.01)
*B01J 23/58* (2006.01)
*C10G 35/06* (2006.01)
*C07C 5/373* (2006.01)

(52) U.S. Cl. ................ 502/185; 502/300; 502/325; 502/328; 208/137; 208/138; 585/252

(58) Field of Classification Search ........... 502/185, 502/300, 325, 328; 208/137, 138; 585/252
See application file for complete search history.

(56) References Cited

U.S. PATENT DOCUMENTS

| 3,998,900 | A | | 12/1976 | Wilhelm | |
|---|---|---|---|---|---|
| 5,356,851 | A | * | 10/1994 | Sarrazin et al. | 502/185 |
| 5,905,180 | A | * | 5/1999 | Yokoyama et al. | 585/658 |
| 6,177,381 | B1 | * | 1/2001 | Jensen et al. | 502/325 |
| 6,182,443 | B1 | * | 2/2001 | Jarvis et al. | 60/274 |
| 6,187,984 | B1 | * | 2/2001 | Wu et al. | 585/660 |
| 6,245,220 | B1 | * | 6/2001 | Didillon et al. | 208/144 |
| 6,486,370 | B1 | * | 11/2002 | Rende et al. | 585/444 |
| 6,627,578 | B2 | * | 9/2003 | Xu et al. | 502/331 |
| 6,977,067 | B2 | * | 12/2005 | Hwang et al. | 423/651 |
| 2004/0063577 | A1 | * | 4/2004 | Wieland et al. | 502/339 |

FOREIGN PATENT DOCUMENTS

| EP | 0 094 684 A2 | 11/1983 |
|---|---|---|
| EP | 0 166 359 A2 | 1/1986 |
| EP | 0 638 534 A1 | 2/1995 |
| EP | 0 749 799 A1 | 12/1996 |
| EP | 1 151 790 A1 | 11/2001 |
| WO | WO-94/05608 | 3/1994 |

OTHER PUBLICATIONS

H. Armendáriz et al., "Isopentane dehydrogenation on Pt-Sn catalysts supported on Al-Mg-O mixed oxides: effects of Al/Mg atomic ratio," *Applied Catalysis A: General*, 211 (2001), pp. 69-80.

* cited by examiner

*Primary Examiner*—J. A. Lorengo
*Assistant Examiner*—Patricia L. Hailey
(74) *Attorney, Agent, or Firm*—RatnerPrestia

(57) ABSTRACT

A catalyst suitable for the dehydrogenation and hydrogenation of hydrocarbons comprises at least one first metal and at least one second metal bound to a support material. The at least one first metal comprises at least one transition metal, suitably a platinum group metal. The support material is provided with an overlayer such that acidic sites on the support material are substantially blocked. In a preferred embodiment the catalyst is also substantially chloride free. Method of preparing catalyst are also disclosed.

19 Claims, No Drawings

CATALYST

This application is the U.S. national phase application of PCT International Application No. PCT/GB02/03218.

This invention relates to improved catalysts, in particular it relates to improved supported catalysts suitable for the dehydrogenation and hydrogenation of hydrocarbons, and to methods for their production.

Of the known catalysts for the dehydrogenation and the hydrogenation of hydrocarbons, among the most effective are those prepared by supporting a platinum group metal (PGM) and an element from Group IV of the periodic table on a high surface area metal oxide support. It is important that the PGM and the Group IV element are well interdispersed on the surface of the support. To achieve this requires the use of suitable precursors, which are applied as solutions to the support, before thermally treating the resulting materials to form the active catalysts. In practice, because of the low solubility and poor mutual miscibility of many available precursors, the desired high interdispersion required is difficult to achieve. Chloride salts are often the only precursors of practical use. However, the use of chloride salts has a detrimental effect on the catalysts. Chloride ions on the support surface can lead to the occurrence of undesired reactions, such as isomerisation, carbon deposition and methane formation. To compound the problem, high surface area supports often contain adventitious electron-withdrawing (acidic) species or sites, which can have the same detrimental effect as chloride ions.

EP 0 166 359 discloses a process for the dehydrogenation of a feedstock containing isobutane, n-butane and butadiene using a steam activated catalyst. Three types of catalyst are described, all of which are based on a highly calcined spinel support. The first catalyst type is produced by impregnating the support with a PGM solution, e.g. chloro-platinic acid; the second catalyst type includes a further impregnation with a Group IA metal solution; and the third type adds a yet further impregnation with a solution of tin, germanium or lead. Chloride containing solutions are preferred. The impregnation treatments may be carried out in any order or all at once.

EP 0 094 684 discloses a process whereby a noble metal catalyst is applied to a support such that the metal remains only at the surface of the support. This is said to be achieved by impregnating a support with a platinum sulphite complex. Preferred supports include zinc aluminates. The catalysts so prepared are suitable for the dehydrogenation of butane.

In accordance with a first aspect of the present invention, a catalyst suitable for the dehydrogenation and hydrogenation of hydrocarbons comprises at least one first metal and at least one second metal bound to a support material; wherein the at least one first metal comprises at least one transition metal; and wherein the support material is provided with an overlayer such that acidic sites on the support material are substantially blocked.

Blocking of the acidic sites, which are inherently present on the surface of for example, metal oxide supports, improves the selectivity of the catalysts and reduces or substantially prevents the occurrence of unwanted side reactions. Acidic sites can 'crack' hydrocarbons, to produce unwanted methane, and can also cause hydrocarbons to form aromatic molecules, which in turn can lead to rapid catalyst deactivation by forming carbon deposits on the catalyst. This process of catalyst deactivation is known as 'coking'.

Contrastingly, in EP 0 166 359 there is no specified order in which the components should be impregnated onto the supports. The formation of an overlayer is not taught, thus acidic sites on the support will remain available to interfere with the catalytic reaction.

In a preferred embodiment, the catalyst is substantially chloride free.

The catalysts so produced show improved selectivity, minimising the production of unwanted reaction products. In addition to optimising the yield of a desired product, improved selectivity reduces coking, leading to significantly increased catalyst lifetimes. One example of a process which benefits from the use of catalysts according to the present invention is the dehydrogenation of ethane to yield ethylene. Current state of the art supported PGM catalysts produce considerably larger quantities of unwanted methane than they do ethylene, whereas using the catalysts of the present invention the majority of the product is ethylene. The practical and economic advantages of this are clear.

Often during processes for the catalytic dehydrogenation and hydrogenation of hydrocarbons (see for example EP 0 166 359), steam is added to suppress carbon formation which would otherwise render the catalyst ineffective. Steam generation consumes energy, and thus adds further cost and complication to the process. A further advantage of the catalysts of the present invention is that steam is not required for such processes.

In accordance with a second aspect of the present invention, a method of making a catalyst suitable for the dehydrogenation and hydrogenation of hydrocarbons comprises the steps of:

(a) contacting a support material with a solution of an overlayer precursor, (b) drying and calcining the support material to form an overlayer, (c) contacting the calcined support material with a solution of at least one first metal precursor and at least one second metal precursor; and (d) drying and calcining the as treated support material to form the catalyst;

wherein the overlayer comprises a metal oxide which is more basic than the support material such that acidic sites on the support material are substantially blocked.

Preferably, the overlayer is more basic than the support material, and more preferably the overlayer is substantially non-acidic. Suitably, the overlayer comprises a layer of tin oxide, germanium oxide, lead oxide, copper oxide, zinc oxide, gallium oxide, lanthanum oxide, barium oxide or any mixture thereof. In a preferred embodiment, the overlayer comprises a layer of tin oxide. The overlayer may be deposited from a solution of an overlayer precursor, which may comprise any soluble salt of the desired metal. For example, a solution of $SnCl_2.2H_2O$ in hydrochloric acid is suitable as an overlayer precursor for the formation of a tin oxide overlayer. After immersion in the solution for ca. 2 hours, the support material may be dried in air, for example for ca. 8–12 hours at 120° C., before being calcined in air at ca. 500° C for between ca. 4–8 hours. These processing times and temperatures are not prescriptive and can be altered as would be known to the skilled man, without departing from the scope of the present invention.

Platinum group metals are known to be particularly effective at catalysing the dehydrogenation and hydrogenation of hydrocarbons and preferably, the at least one first metal comprises a transition metal chosen from the group; platinum, palladium, rhodium, ruthenium, iridium and osmium. Suitably, the at least one first metal precursor is a salt of platinum, palladium, rhodium, ruthenium, iridium or osmium.

Preferably, the at least one second metal is tin, although germanium, lead, gallium, copper, zinc, antimony and bismuth may also be used. Preferably, the at least one second metal precursor comprises a salt of tin, germanium, lead, gallium, copper, zinc, antimony or bismuth, with a salt of tin being particularly preferred.

In some embodiments of the invention, the second metal may be the same as that used to form the overlayer. For example, a tin oxide overlayer may be used with a second metal comprising tin. It will be understood that the functions of the two sources of e.g. tin, are distinct. As described hereinbefore, the overlayer blocks the acidic sites on the support to prevent unwanted side reactions, whilst the second enhances the catalytic activity of the transition metal, e.g. platinum.

It is simplest to co-deposit both the first metal and the second metal from the same solution as this requires fewer process steps. There is also the benefit that if only a single solution is used, the interdispersion of the metallic species is improved. It will be clear however that individual solutions of each species may be used if desired, although the catalysts so produced may be less effective.

Preferably, the solution (or solutions) of the at least one first metal precursor and the at least one second metal precursor is (are) free from chloride. More preferably, the at least one first metal precursor comprises an anionic carboxylate for example, acetate, oxalate, or tartrate, and the at least one second metal precursor comprises an anion of $BF_4^-$.

In a particularly preferred embodiment, the solution of the at least one first metal precursor and the at least one second metal precursor comprises $K_2[Pt(C_2O_4)_2]$ and $Sn(BF_4)_2$ in an aqueous solution of citric acid.

The use of $BF_4^-$ results in the formation of complex ions of $BF^-$ on the surface of the catalyst. These complex anions are believed to have the following beneficial effects during hydrogen removal and hydrogen addition reactions:
(i) They create an electronegative environment, which promotes desorption of the desired products and,
(ii) They hinder the occurrence of side reactions which lead to the deposition of carbon on the catalyst (coking).

Preferably, the support material is at least one of an oxide, carbide or sulphide of a metal or non-metal; carbon; or any mixture or solid solution thereof. More preferably, the support material is at least one metal oxide chosen from the group; alumina, spinels, silica, magnesia, thoria, zirconia and titania. If desired, suitable oxides may be obtained via the thermal treatment of minerals such as hydrotalcites.

The support material may take any physical form but, to maximise the active surface area, it is preferably in a finely divided form. In one embodiment, the support may be formed into a slurry and the slurry used as a washcoat to provide a catalyst coating to any suitable structure, for example a bulk ceramic, metal or other solid structure If desired, the catalyst may further comprise a catalyst promoter. Suitable catalyst promoters include the alkali metals; lithium, sodium, potassium, rubidium and caesium. The catalyst promoter may be incorporated into the catalyst via a separate processing step for example, by treatment with an alkali metal salt however preferably, the catalyst promoter is incorporated as a cation in the at least one first metal precursor. For example, potassium is incorporated as a catalyst promoter when $K_2[Pt(C_2O_4)_2]$ is used as a first metal precursor. In addition to reducing further the overall acidity of the catalyst, the presence of an alkali metal as a catalyst promoter can block sites on the metal surface that are active for undesired side reactions.

The catalysts of the present invention are suitable for the hydrogenation and dehydrogenation of any hydrocarbon species. Some non-limiting examples include hydrogenation reactions such as those to convert unsaturated hydrocarbons to less saturated or fully saturated hydrocarbons; and dehydrogenation reactions such as the conversion of ethane to ethylene, propane to propylene, isobutane to isobutylene or ethylbenzene to styrene. The reactant hydrocarbon may be provided in a pure form, be carried by a diluent such as nitrogen or hydrogen, or be combined with air or oxygen, or in any manner as is known in the art.

The invention will now be described by way of example only.

EXAMPLE 1

Preparation of Benchmark Catalyst, Not According to the Invention

A catalyst with nominal composition (by weight) of 1.5% Pt-1.5% Sn/$Al_2O_3$ was prepared (using the method disclosed by FC Wilhelm in U.S. Pat. No. 3,998,900) by impregnating γ-$Al_2O_3$ with an aqueous complex, formed by mixing chloroplatinic acid with an acidified solution of tin(II) chloride. The resultant material was dried (110° C.; air; 24 hr) and calcined (500° C.; air; 2 hr).

EXAMPLE 2

Preparation of Pt—Sn Catalyst with Tin Oxide Overlayer on Spinel Support 10 g of a catalyst with nominal composition 1.5% Pt-1.5% Sn/7.5% Sn—$MgAl_2O_4$ was prepared by (i) forming the magnesium aluminate spinel, (ii) depositing a tin oxide overlayer on the spinel, (iii) impregnating with a Pt—Sn complex.

In detail, 17.95 g $Mg(NO_3)_2.6H_2O$ and 52.52 g $Al(NO_3)_3.9H_2O$ were dissolved in 1 $dm^3$ of deionised water. The pH of the solution was adjusted to 10 by addition of aqueous $NH_4OH$. This caused the formation of a white precipitate, which was isolated and washed several times with hot deionised water to remove any residual traces of $NH_4NO_3$. The solid was dried in air at 120° C. for 8 hours and finally calcined in air at 800° C. for 16 hours. X-ray diffraction analysis of this solid confirmed that $MgAl_2O_4$ had formed. 1.5 g $SnCl_2.2H_2O$ was dissolved in 6 $cm^3$ 0.1 M aqueous HCl at 0° C. and contacted with the $MgAl_2O_4$ for 2 hours. The material was dried in air at 120° C. for 8 hours and subsequently calcined in air at 500° C. for 4 hours. 0.29 g $SnCl_2.2H_2O$ was dissolved in 6 $cm^3$ 0.1 M aqueous HCl solution at 0° C. 0.38 g chloroplatinic acid was added to the acidified $SnCl_2.2H_2O$, and the solution took on a deep red colour consistent with the formation of the $[PtCl_2(SnCl_3)_2]^{2-}$ complex. This solution was contacted with the 7.5% Sn—$MgAl_2O_4$ material for 2 hours prior to drying in air at 120° C. for 8 hours. Calcination in air at 500° C. for 4 hours yielded the final catalyst.

EXAMPLE 3

Preparation of Chloride-free Catalyst Containing Pt—Sn on Alumina Support 5 g of catalyst with nominal composition 1.5% Pt-1.5% Sn/$\theta$-Al$_2$O$_3$ was prepared by impregnating a low-acidity alumina ($\theta$-Al$_2$O$_3$) with a Pt—Sn complex, which had been formed from a non-chloride precursor of Pt and a non-chloride precursor of Sn.

In detail, 5 g $\theta$-Al$_2$O$_3$ was dried at 300° C. in air and cooled to room temperature in a desiccator to ensure complete evacuation of the pore structure. 0.18 g K$_2$[Pt$^{II}$(C$_2$O$_4$)$_2$] was added to 7 cm$^3$ 100 g l$^{-1}$ aqueous citric acid, and warmed until the solution formed took on a lime green colour.

0.38 g Sn(BF$_4$)$_2$ (50% aqueous solution) was added to this solution and a dark red colour was seen to develop. The solution was allowed to cool to room temperature and contacted with the support for 2 hours, prior to drying in air at 120° C. overnight and final calcination in air at 500° C. for 4 hrs.

EXAMPLE 4

Preparation of Chloride-free Catalyst Containing Pt—Sn on Spinel Support 5 g of catalyst with nominal composition 1.5% Pt-1.5% Sn/MgAl$_2$O$_4$ was prepared by forming the magnesium aluminate spinel (as described in Example 2), and then impregnating it with a chloride-free Pt—Sn complex (as described in Example 3). The impregnated spinel was dried in air at 120° C. for 8 hrs, and calcined in air at 500° C. for 4 hrs.

EXAMPLE 5

Performance of Catalysts

The catalysts were tested using a process for ethane dehydrogenation, disclosed by BM Maunders and SR Partington in WO 9405608, in which a dehydrogenation catalyst is combined with a hydrogen removal material. The presence of the hydrogen removal material is intended to increase the yield of ethylene, above the value normally reached when the forward (dehydrogenation) and reverse (re-hydrogenation) reactions are allowed to reach equilibrium.

In each test, 1 g catalyst was mixed with 3 g hydrogen-removal material. The mixture was packed in a cylindrical reactor, which was heated to 500° C. An undiluted flow of ethane (20 cm$^3$ min$^{-1}$) was passed through the reactor for 2 minutes, during which time all the exit gas was collected and analysed. The procedure was repeated until the hydrogen storage material became saturated, and the ethylene yield returned to the normal equilibrium value (3.7% at 500° C.). The hydrogen storage material could be regenerated by passing air through the reactor.

Table 1 shows the molar conversion of ethane, the molar selectivity to ethylene and the molar yield of ethylene for each of the catalysts according to the present invention (Examples 2 to 4) and for the prior art catalyst (Example 1). The values are averages, based on several 2 minute exposures to ethane, both before the hydrogen removal material had become saturated and after it had been regenerated. In all cases, the ethylene yield exceeded the normal equilibrium yield. Although the prior art catalyst (Example 1) was the most active in terms of percentage conversion, it wasted most of the ethane by converting it to methane. Each of the formulations according to the invention showed substantially higher selectivity to ethylene, with the most selective being the catalyst made by impregnating a low-acid support material with a chloride-free Pt—Sn complex (Example 3).

TABLE 1

Ethane dehydrogenation

| Catalyst | Conversion % | Selectivity % ethylene | Yield % ethylene |
|---|---|---|---|
| Example 1 (Prior art) | 49 | 11 | 5.5 |
| Example 2 | 26 | 71 | 18 |
| Example 3 | 25 | 80 | 20 |
| Example 4 | 19 | 84 | 16 |

EXAMPLE 6

Catalyst with a Lanthanum Oxide Over Layer

A benchmark catalyst (not according to the invention) with a nominal composition of 1% Pt-1% Sn/Al$_2$O$_3$ was prepared according to example 1. A further catalyst according to the invention was prepared in an analogous fashion but using an alumina support onto which La$_2$O$_3$ had been deposited to form an overlayer. The nominal composition of this catalyst was 1% Pt-1% Sn/10% La$_2$O$_3$/Al$_2$O$_3$. After impregnation, the catalyst was dried at 100° C. in air for 24 hours prior to air calcining at 500° C. for 2 hours.

Both catalysts were tested using a process for oxidative dehydrogenation of alkanes, disclosed by S. E. Golunski and J. W. Hayes in EP 0638534 B1. Isobutane (50 cm$^3$ min$^{-1}$) at a temperature of 500° C. was passed through a cylindrical reactor, packed with 0.5 g of catalyst. When the catalyst bed temperature began to drop, at the onset of dehydrogenation, just enough air was added to the isobutane to achieve thermally-neutral operation (i.e. bed temperature=gas inlet temperature).

After 2 minutes of oxidative dehydrogenation, when the first measurements were made, the yield of isobutene was the same (30%) both for the benchmark catalyst and for the catalyst with the La$_2$O$_3$ overlayer. However, the subsequent rate of de-activation was higher for the benchmark catalyst. It took 90 minutes for the isobutene yield to drop from 30% to 20% for the benchmark catalyst, but it took twice as long for the catalyst with the La$_2$O$_3$ overlayer to de-activate by the same amount.

The invention claimed is:

1. A catalyst suitable for the dehydrogenation and hydrogenation of hydrocarbons, the catalyst consisting essentially of:
   a support material;
   an overlayer disposed on the support material;
   at least one first metal; and
   at least one second metal, said first and second metals bound to the overlayer;
   wherein the at least one first metal comprises at least one transition metal selected from the group consisting of platinum, palladium, rhodium, ruthenium, iridium and osmium; the at least one second metal selected from the group consisting of tin, germanium, lead, gallium, zinc, antimony and bismuth; and wherein the overlayer comprises a layer of tin oxide, germanium oxide, lead oxide, zinc oxide, gallium oxide, lanthanum oxide, barium oxide or any mixture thereof, such that acidic sites on the support material are substantially blocked.

2. A catalyst according to claim 1, wherein the catalyst is substantially chloride free.

3. A catalyst according to claim 1, wherein the support material comprises at least one of an oxide, carbide or sulphide of a metal or non-metal; carbon; or any mixture or solid solution thereof.

4. A catalyst according to claim 3, wherein the support material comprises at least one metal oxide chosen from the group consisting of alumina, spinels, silica, magnesia, thoria, zirconia and titania.

5. A catalyst suitable for the dehydrogenation and hydrogenation of hydrocarbons, the catalyst consisting essentially of:
   a support material;
   an overlayer disposed on the support material;
   at least one first metal;
   at least one second metal, wherein said first and second metals are bound to the overlayer;
   and
   a catalyst promoter;
wherein the at least one first metal comprises at least one transition metal selected from the group consisting of platinum, palladium, rhodium, ruthenium, iridium and osmium; the at least one second metal is selected from the group consisting of tin, germanium, lead, gallium, zinc, antimony and bismuth; and wherein the overlayer comprises a layer of tin oxide, germanium oxide, lead oxide, zinc oxide, gallium oxide, lanthanum oxide, barium oxide or any mixture thereof, such that acidic sites on the support material are substantially blocked.

6. A catalyst according to claim 5, wherein the catalyst promoter comprises an alkali metal.

7. A method of making a catalyst suitable for the dehydrogenation and hydrogenation of hydrocarbons, the method comprising the steps of:
   (a) contacting a support material with a solution of an overlayer precursor;
   (b) drying and calcining the support material to form an overlayer;
   (c) contacting the calcined support material from step (b) with a solution of at least one first metal precursor and at least one second metal precursor; and
   (d) drying and calcining the treated support material from step (c) to form the catalyst;
wherein the overlayer comprises a layer of tin oxide, germanium oxide, lead oxide, zinc oxide, gallium oxide, lanthanum oxide, barium oxide or any mixture thereof such that acidic sites on the support material are substantially blocked wherein the at least one first metal precursor consists of a salt of platinum, palladium, rhodium, ruthenium, iridium or osmium; and the at least one second metal precursor consists of a salt of tin, germanium, lead, gallium, copper, zinc, antimony or bismuth.

8. A method according to claim 7, wherein the at least one first metal precursor comprises an anionic carboxylate.

9. A method according to claim 7, wherein the at least one second metal precursor comprises an anion of $BF_4^-$.

10. A method according to claim 7, wherein the solution of at least one first metal precursor and at least one second metal precursor comprises $K_2[Pt(C_2O_4)_2]$ and $Sn(BF_4)_2$ in an aqueous solution of citric acid.

11. A method of making a catalyst suitable for the dehydrogenation and hydrogenation of hydrocarbons, the method comprising the steps of:

(a) contacting a support material with a solution of at least one first metal precursor and at least one second metal precursor; and
(b) drying and calcining the as treated support material from step (a) to form the catalyst;
wherein the solution of the at least one first metal precursor and the at least one second metal precursor comprises $K_2[Pt(C_2O_4)_2]$ and $Sn(BF_4)_2$ in an aqueous solution of citric acid.

12. A method of hydrogenating a hydrocarbon, the method comprising the step of contacting the hydrocarbon with a hydrogen-containing gas and a catalyst comprising at least one first metal and at least one second metal bound to a support material; wherein the at least one first metal comprises at least one transition metal selected from the group consisting of platinum, palladium, rhodium, ruthenium, iridium and osmium; the at least one second metal is selected from the group consisting of tin, germanium, lead, gallium, zinc, antimony and bismuth; and wherein the support material is provided with an overlayer comprising a layer of tin oxide, germanium oxide, lead oxide, zinc oxide, gallium oxide, lanthanum oxide, barium oxide or any mixture thereof, such that acidic sites on the support material are substantially blocked.

13. A method of dehydrogenating a hydrocarbon, the method comprising the step of contacting the hydrocarbon with a catalyst comprising at least one first metal and at least one second metal bound to a support material; wherein the at least one first metal comprises at least one transition metal chosen from the group consisting of platinum, palladium, rhodium, ruthenium, iridium and osmium; the at least one second metal is chosen from the group consisting of tin, germanium, lead, gallium, zinc, antimony and bismuth; and wherein the support material is provided with an overlayer comprising a layer of tin oxide, germanium oxide, lead oxide, zinc oxide, gallium oxide, lanthanum oxide, barium oxide or any mixture thereof, such that acidic sites on the support material are substantially blocked.

14. A method of making a catalyst suitable for the dehydrogenation and hydrogenation of hydrocarbons, the method comprising the steps of:
   (a) contacting a support material with a solution of an overlayer precursor;
   (b) drying and calcining the support material to form an overlayer;
   (c) contacting the calcined support material from step (b) with a solution of at least one first metal precursor comprising an anionic carboxylate and at least one second metal precursor; and
   (d) drying and calcining the treated support material from step (c) to form the catalyst;
wherein the overlayer comprises a layer of tin oxide, germanium oxide, lead oxide, zinc oxide, gallium oxide, lanthanum oxide, barium oxide or any mixture thereof such that acidic sites on the support material are substantially blocked wherein the at least one first metal precursor consists of a salt of platinum, palladium, rhodium, ruthenium, iridium or osmium; and the at least one second metal precursor consists of a salt of tin, germanium, lead, gallium, copper, zinc, antimony or bismuth.

15. A method according to claim 14, wherein the at least one second metal precursor comprises an anion of $BF_4^-$.

16. A method according to claim 14, wherein the solution of at least one first metal precursor and at least one second metal precursor comprises $K_2[Pt(C_2O_4)_2]$ and $Sn(BF_4)_2$, in an aqueous solution of citric acid.

17. A method of making a catalyst suitable for the dehydrogenation and hydrogenation of hydrocarbons, the method comprising the steps of:
(a) contacting a support material with a solution of an overlayer precursor;
(b) drying and calcining the support material to form an overlayer;
(c) contacting the calcined support material from step (b) with a solution of at least one first metal precursor and at least one second metal precursor comprising an anion of $BF_4^-$; and
(d) drying and calcining the treated support material from step (c) to form the catalyst;
wherein the overlayer comprises a layer of tin oxide, germanium oxide, lead oxide, zinc oxide, gallium oxide, lanthanum oxide, barium oxide or any mixture thereof such that acidic sites on the support material are substantially blocked wherein the at least one first metal precursor consists of a salt of platinum, palladium, rhodium, ruthenium, iridium or osmium; and the at least one second metal precursor consists of a salt of tin, germanium, lead, gallium, copper, zinc, antimony or bismuth.

18. A method according to claim 17, wherein the at least one first metal precursor comprises an anionic carboxylate.

19. A method according to claim 17, wherein the solution of at least one first metal precursor and at least one second metal precursor comprises $K_2[Pt(C_2O_4)_2]$ and $Sn(BF_4)_2$ in an aqueous solution of citric acid.

* * * * *